United States Patent
Park

(10) Patent No.: US 7,479,620 B2
(45) Date of Patent: Jan. 20, 2009

(54) HEATER AND THE METHOD FOR PRODUCING THE SAME USING PCB

(76) Inventor: Jae-Sang Park, #107-2009 Hyundae Apt., 1344, Bangbae dong, Scocho-gu, Seoul, 137-937 (KR)

( * ) Notice: Subject to any disclaimer, the term of this patent is extended or adjusted under 35 U.S.C. 154(b) by 383 days.

(21) Appl. No.: 10/572,119

(22) PCT Filed: Sep. 17, 2004

(86) PCT No.: PCT/KR2004/002396

§ 371 (c)(1),
(2), (4) Date: Mar. 16, 2006

(87) PCT Pub. No.: WO2005/027579

PCT Pub. Date: Mar. 24, 2005

(65) Prior Publication Data

US 2007/0062925 A1    Mar. 22, 2007

(51) Int. Cl.
*H05B 3/02* (2006.01)
*F27D 11/00* (2006.01)

(52) U.S. Cl. ............... 219/538; 219/536; 219/537; 219/388; 219/541; 219/542; 219/203

(58) Field of Classification Search ............ 219/536–8, 219/388, 541–2, 203
See application file for complete search history.

(56) References Cited

U.S. PATENT DOCUMENTS 6,593,249 B2 * 7/2003 Meyer et al. .............. 438/759
6,754,551 B1 * 6/2004 Zohar et al. .............. 700/121

\* cited by examiner

*Primary Examiner*—Shawntina Fuqua
(74) *Attorney, Agent, or Firm*—Park Law Firm; John K. Park

(57) ABSTRACT

Disclosed a heater and a method for manufacturing the heater using a PCB process for providing a heater generating heat at a temperature that is proper to use by designing the heater having an accurate resistance using the PCB process on an insulated board. The inventive method comprises the steps of: forming a thin plate by coating substance that generates heat according to power supply on one side of an insulated board; forming a masking pattern on an upper side of the insulated board, the masking pattern forming circuit patterns designed to have a heating resistor designed to have a constant resistance, a the power supply terminal for supplying power to the heating resistor, a joining terminal of a sensor mount to which a sensor for measuring a heating temperature about a predetermined region of the heating resistor is mounted, and a sensor connecting terminal for causing the outside to read the temperature measured from the sensor, etching to erode the insulated board that is formed with the masking pattern and generate the heater having the circuit patterns; and forming a insulating protecting film for protecting the patterns that are formed on the upper side of the insulated board.

12 Claims, 4 Drawing Sheets

HEATER AND THE METHOD FOR PRODUCING THE SAME USING PCB

TECHNICAL FIELD

This invention relates to a heater and a method for manufacturing the heater using a PCB process, and more particularly to a heater and a method for manufacturing the heater using a PCB process for providing a heater generating heat at a temperature that is proper to use by designing the heater having an accurate resistance using the PCB process on an insulated board.

Specially, the invention relates to a heater and a method for manufacturing the heater using a PCB process for easily installing a temperature sensor on a region where a heating temperature is measured by forming a chip mount that can be joined with a sensor for sensing the heating temperature of the heater on a desired location when designing the heater.

Further, the invention relates to a heater and a method for manufacturing the heater using a PCB process for using as a temperature sensor as well as providing a function of the heater by forming thermoelectric couple on a PCB using two different substances having high thermoelectromotive forces, respectively.

Further, the invention relates to a heater and a method for manufacturing the heater using a PCB process for realizing at least one circuit using single PCB, thereby making a device adopting the PCB compact and slim.

BACKGROUND ART

There have been known a heater having a nichrome wire with electric

There have been known a heater having a NI-Cr wire with electric resistance that connected to an electric wire and a film heater constituted by connecting an electric wire to an end of a heating wire such as a heater attached to a rear window of a car as conventional heaters using electricity.

However, according to the conventional heaters, there has been a problem in that, since most of the heaters are manufactured by a method that cuts out in a film status, it is difficult to integrate a terminal for supplying power or a sensing terminal for sensing the temperature of the heater to the heater.

Further, there has been a problem in that, in case of making an electric resistance low, which determines a heating level in the conventional electric heaters, it is difficult to accurately generate the resistance thereof.

DISCLOSURE OF THE INVENTION

Therefore, the invention has been made in view of the above problems, and it is an object of the invention to provide a heater and a method for manufacturing the heater using a PCB process for providing a heater that generates heat at a temperature that is proper to use by designing the heater having an accurate resistance using a PCB process on an insulated board.

Further, another object of the invention is to provide a heater and a method for manufacturing the heater using a PCB process for easily installing a temperature sensor on a region where a heating temperature is measured by forming a chip mount that can be joined with a sensor for sensing a heating temperature of the heater on a desired location when designing the heater.

Further, another object of the invention is to provide a heater and a method for manufacturing the heater using a PCB process for using as a temperature sensor as well as providing a function of the heater by forming thermoelectric couple on single PCB using two different substances having high thermoelectromotive forces, respectively.

Further, another object of the invention is to provide a heater and a method for manufacturing the heater using a PCB process for realizing at least one circuit using single PCB, thereby making a device adopting the PCB compact and slim.

To accomplish the objects of the invention, in one embodiment of the invention, a method for manufacturing a heater comprises the steps of: forming a thin plate by coating substance that generates heat according to power supply on one side of an insulated board; forming a masking pattern on an upper side of the insulated board, the masking pattern forming circuit patterns designed to have a heating resistor designed to have a constant resistance, a the power supply terminal for supplying power to the heating resistor, a joining terminal of a sensor mount to which a sensor for measuring a heating temperature about a predetermined region of the heating resistor is mounted, and a sensor connecting terminal for causing the outside to read the temperature measured from the sensor; etching to erode the insulated board that is formed with the masking pattern and generate the heater having the circuit patterns; and forming a insulating protecting film for protecting the patterns that are formed on the upper side of the insulated board.

At this time, the circuit pattern that is formed on the upper side of the insulated board is determined by the equation:

$$R = \rho L/A$$

where, $\rho$ is specific resistance of the heating resistor, L is length, and A is cross-sectional area.

Further, the step of forming the circuit patterns further comprises the step of forming circuit patterns different from the circuit pattern of the heating resistor on one side formed with the patterns and the other side, respectively.

In a further embodiment of the invention, a heater comprises: an insulated board; a heating resistor for generating heat with the amount of heat previously designed according to power supply, the heating resistor being formed by a circuit pattern designed to have a constant resistance on an upper side of the insulated board; a power supply terminal for supplying the heating resistor with electric power; a sensor mount that is mounted with a sensor for measuring heating temperature about a predetermined region of the heating resistor; a sensor connecting terminal which is connected with the joining terminal to cause the outside to read the measured temperature; and an insulating protection film for protecting the heating resistor; wherein a heating resistor pattern, a sensor mount joining pattern, and a sensor connecting terminal pattern are formed on an upper side of the insulated board by a masking process and a etching process.

Specially, substance coated on the insulated board is any one selected from the group consisting of copper, steel, nickel, chrome and alloy generated by compounding one substance into one of the above pure metals.

Further, the insulated board is coated with two different substances having high thermoelectromotive forces to form a heating resistor, respectively. The heating resistor generates heat according to whether power is supplied or not and forms thermoelectric couple. The insulated board is formed with a via hole for connecting the different substances.

Further, the upper side and the lower side of the insulated board are coated with two different substances having high thermoelectromotive forces to form a heating resistor, respectively. The heating resistor generates heat according to whether power is supplied or not and forms thermoelectric couple. The insulated board is formed with a via hole for connecting the different substances.

BRIEF DESCRIPTION OF THE DRAWINGS

The above and other objects and features of the invention will become apparent from the following description of preferred embodiments taken in conjunction with the accompanying drawings, in which.

BEST MODES FOR CARRYING OUT THE INVENTION

The invention will be described in further detail by way of preferred embodiments with reference to the accompanying drawings.

Figure 1:
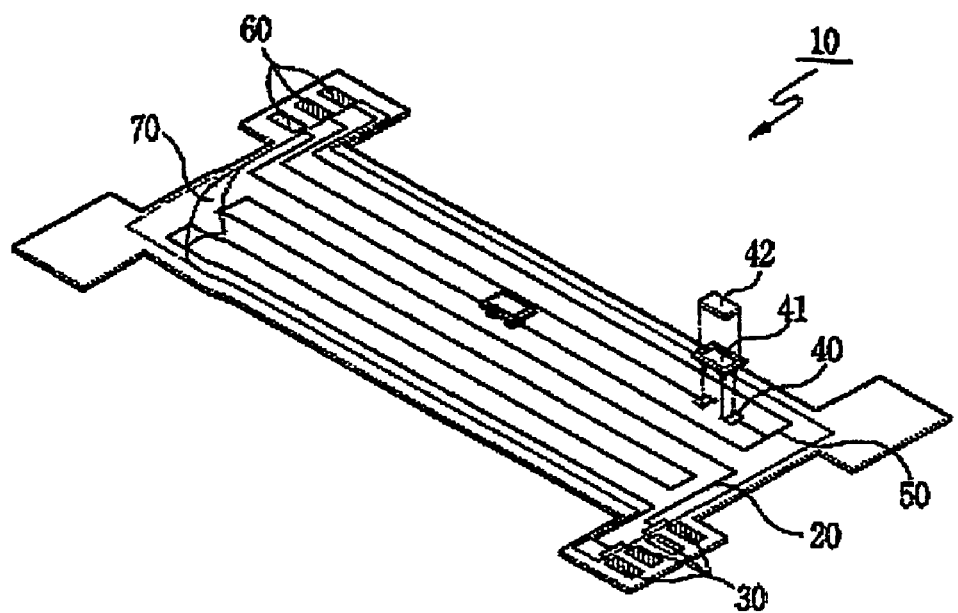
FIG. 1 is a view for explaining an embodiment of a heater using a PCB process according to the invention.

FIG. 1 is a view for explaining an embodiment of a heater using a PCB process according to the invention.

EXAMPLE 1

Referring to FIG. 1, a heater of the invention comprises an insulated board 10, a heating resistor 20 for generating heat with the amount of heat previously designed according to power supply, which is formed by a circuit pattern designed to have a constant resistance on an upper side of the insulated board 10, a power supply terminal 30 for supplying the heating resistor 20 with electric power, a joining terminal 40 of a sensor mount 41 mounted with a sensor 42 for measuring heating temperature about a predetermined region of the heating resistor 20, a sensor connecting terminal 60 which is connected with the joining terminal to cause the outside to read the measured temperature, and an insulating protection film 70 for protecting the heating resistor 20.

The joining terminal 40 is fixed and joined with the sensor mount 41, and the sensor mount 41 is mounted and joined with the sensor 42.

Meanwhile, the circuit pattern of the heating resistor 20 is determined by the following equation 1. Especially, the pattern of the heating resistor 20 is designed depending on input voltage, current, alternating current or direct current.

$$R = \rho L/A \quad [1]$$

Here, R is a heating resistor, $\rho$ is specific resistance of the heating resistor, L is length, and A is cross-sectional area.

At this time, the specific resistance of the heating resistor 20 depends on material of the heating resistor 20. For example, the specific resistance of Cu is 17.2 n$\Omega$.m, and, the specific resistance of Zn is 59.0 n$\Omega$.m. Here, the specific resistance means a resistance of substance having a length of 1 m and a cross-sectional area of 1 $m^2$ and, a unit thereof is $\Omega$.m. Further, "n" in n$\Omega$.m stands for nano, and means $10^{-9}$. That is, 1 $\Omega.mm^2$/m equals $10^3$ n$\Omega$.m Meanwhile, a substance coated on the insulated board 10 is any one selected from the group consisting of Cu, Fe, Ni, Cr and alloy generated by compounding one substance into one of the above metals in a predetermined proportion. Here, the coating substance is the heating resistor 20 after finishing an etching process, and is used by selecting according to a resistance of the heating resistor 20 to be designed.

EXAMPLE 2

Figure 2:
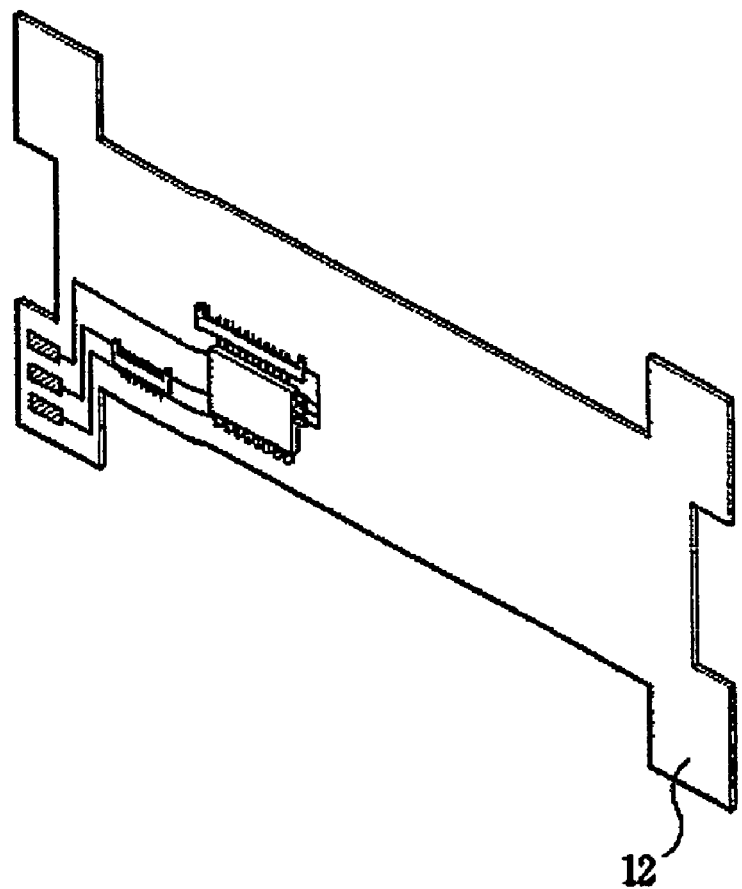
FIG. 2 is a view for showing a lower side of the PCB in FIG. 2.

Further, Referring to FIG. 2, the insulated board 10 is formed with the heater of Embodiment 1 on an upper side 11 thereof, and is provided with control circuits for controlling the heater or control circuit for controlling a device that is mounted with the heater on a lower side 12 thereof. Thus, both sides of PCB may be used.

Meanwhile, although the invention does not show in drawings, it may be realized to have another circuit except for the heater on a margin area in the upper side 11 of the insulated board 10 having the heater like the sensing part of Embodiment 1. That is, single PCB may realize and use at least one circuit, thereby making a device adopting the PCB compact and slim.

EXAMPLE 3

Figure 3:
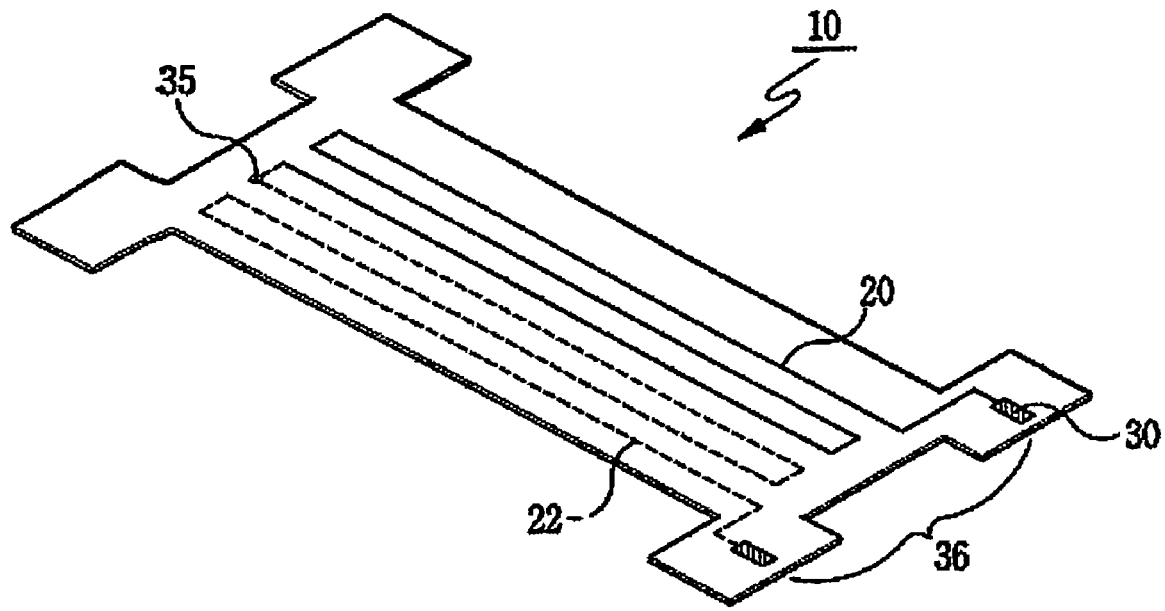
FIG. 3 is a view for explaining a heater and a temperature sensor witch use thermoelectric couple.

Further, referring to FIG. 3, an embodiment that is different from Embodiment 1 according to the invention is shown. That is, two different substances having high thermoelectromotive forces are coated on one side of the insulated board 10, respectively, thereby forming heating resistors 20 and 22. As a result, the heating resistors 20 and 22 simultaneously form heating body and thermoelectric couple. At this time, the above different substances are connected each other by a via hole 35.

EXAMPLE 4

Figure 4:
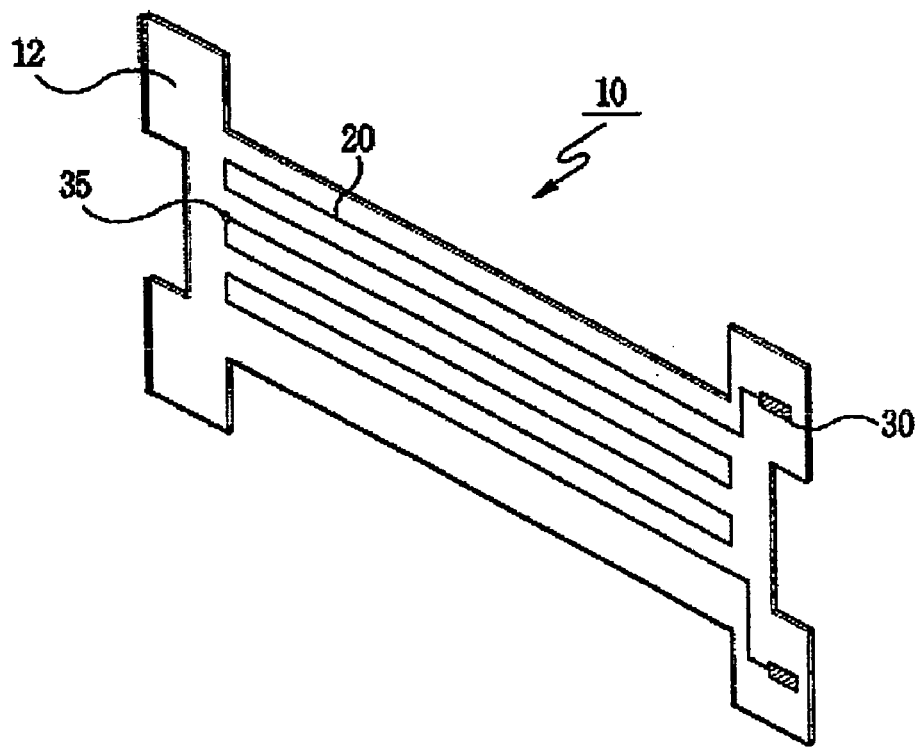
FIGS. 4 and 5 are views for explaining the invention that forms a heater and a temperature sensor by forming heating resistors made of substance forming a thermoelectric couple on an upper side and a lower side of an insulated board, respectively.
Figure 5:
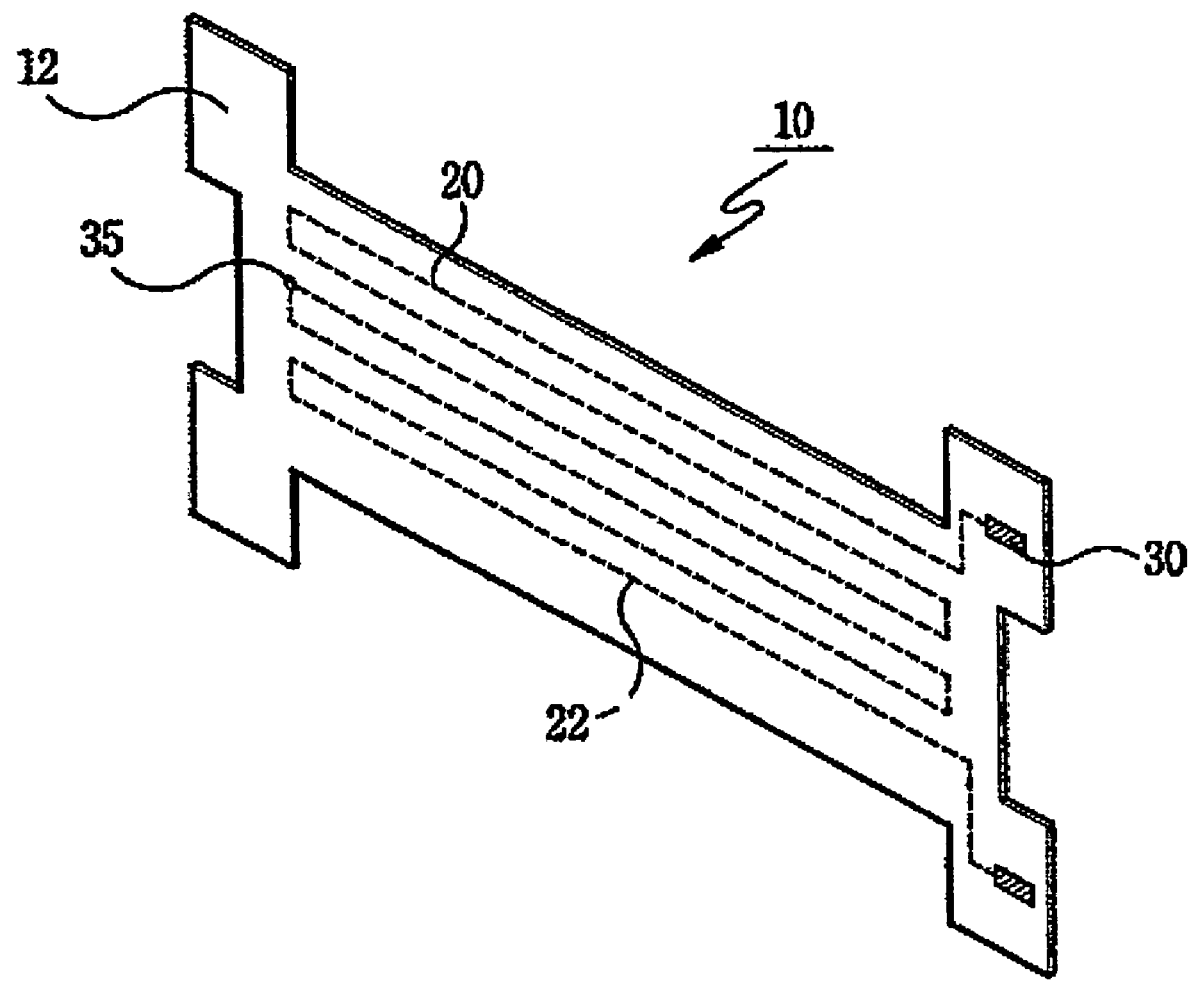

Further, referring to FIGS. 4 and 5, an embodiment that is different from Embodiment 1 according to the invention is shown. That is, two different substances having high thermoelectromotive forces are coated on the upper side 11 and the lower side 12 of the insulated board 10, respectively, thereby forming heating resistors 20 and 22. As a result, the heating resistors 20 and 22 simultaneously form heating body and thermoelectric couple. At this time, there is provided a via hole 35 on the insulated board 10 for connecting the heating resistors 20 and 22 formed on the upper side 11 and the lower side 12, respectively.

From the above, in case of forming thermoelectric couple as described in Embodiments 3 and 4, the temperature of the heater can be automatically controlled. That is, in case of forming thermoelectric couple, if instantaneously turning off power supplied to the heating resistors 20 and 22 and then measuring thermoelectromotive force thereof, the temperature in a contacting portion 35 of thermoelectric couple is measured. If the temperature in the contacting portion 35 of thermoelectric couple, which is measured as described above, is higher than the temperature that is previously set, power supplied to the heating resistors 20 and 22 is turned off. On the contrary, if the temperature measured in the contacting portion of thermoelectric couple is lower than the temperature that is previously set, power is supplied to the heating resistors 20 and 22 to generate heat. At this time, means for supplying power to the heating resistors 20 and 22 uses a switching element such as FET and the like. It is natural that a control device for checking the above temperature and then controlling the switching element should be provided.

Meanwhile, the thermoelectric couple has various kinds according to use. That is, it is broadly classified into noble metal thermoelectric couple and general metal thermoelectric couple, and has various kinds such as platinum-rhodium alloy, platinum rhodium-platinum alloy, chromel-alromel alloy, chromel-constantan alloy, steel-constantan alloy, copper-constantan alloy, and the like. The invention forms the heating resistor by coating the substance forming the thermoelectric couple on the upper side of the insulated board, thereby causing the heating resistor to serve as a temperature sensor as well as a heater.

A method for manufacturing a heater using PCB constituted as described above will be explained hereinafter.

Figure 6:
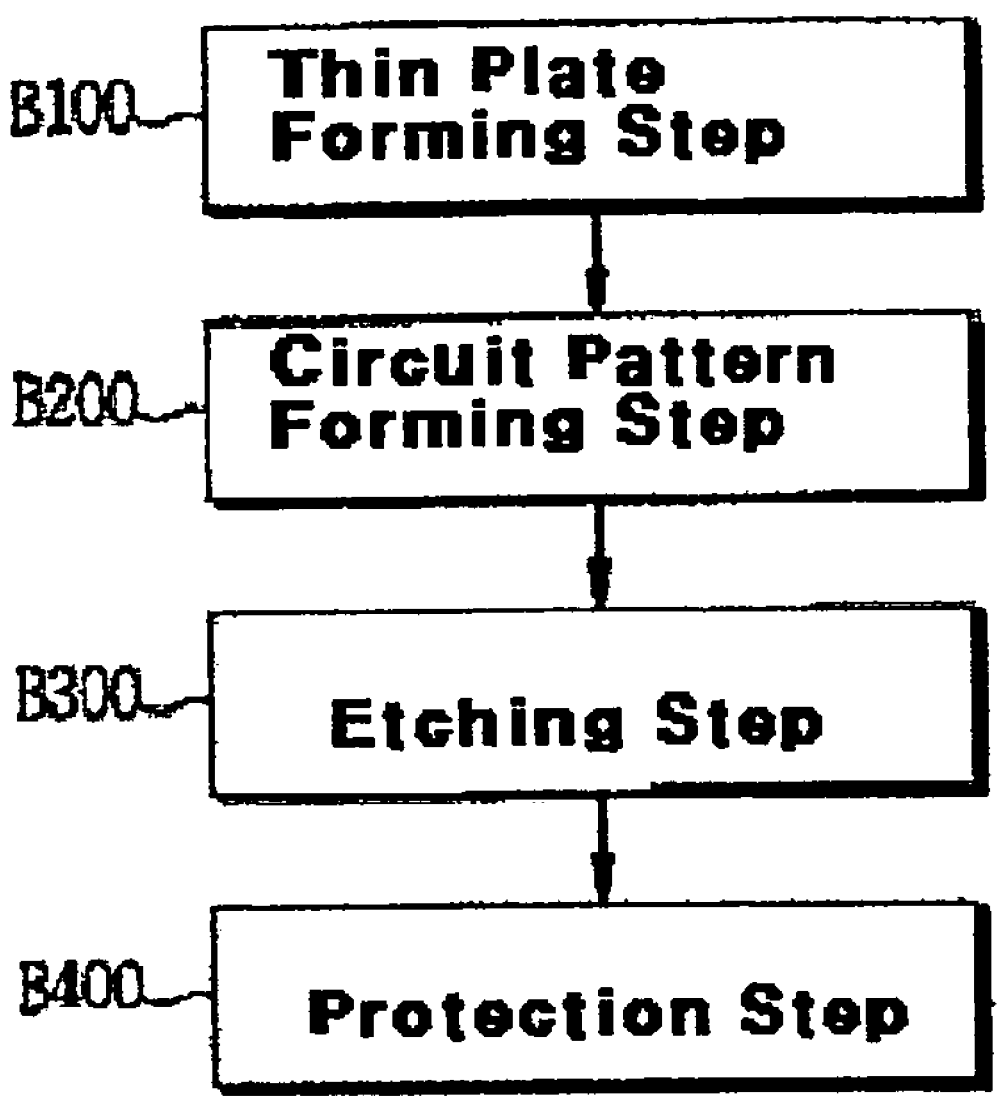
FIG. 6 is a process diagram for explaining a method for manufacturing a heater using a PCB process according to the invention.

First, as shown in FIG. 6, substance that generates heat according to power supply is coated on the one side of the insulated plate 10 to form a thin plate. (B100)

Then, a masking pattern is formed on an upper side of the thin plate that is formed as described above. (B200)

At this time, the masking pattern in the step B200 is formed in the following order; a pattern of the heating resistor 20 that is designed to have a constant resistance, a pattern of the power supply terminal 30 for supplying power to the heating resistor 20, a pattern of the joining terminal 40 that is joined to the sensor mount 41 which the sensor 42 for measuring a heating temperature about a predetermined region of the heating resistor 20 is mounted to, and a pattern of the sensor connecting terminal 60 which is connected with the joining terminal to be read the measured temperature by the outside.

Then, the insulated board 10 that is formed with the masking pattern is dipped into an etching solution for a predetermined time and then the coated substance is eroded and removed except for the masking pattern. As a result, a heater that a user desires is formed on the upper side of the insulated board 10. (B300)

Finally, an insulating protecting film 70 for protecting patterns formed on the upper side of the insulated board is formed. (B400)

Further, the insulated board 10 may use a board made of any one selected from the group consisting of various kinds of materials. Especially, if it uses flexible materials, it may be easily applied to a place such as a side mirror of a car and the like.

The invention is not limited to the above embodiments, and it will be appreciated that any and all changes may accrue to those skilled in the art without departing from the technical spirit of the invention.

INDUSTRIAL APPLICABILITY

From the foregoing, the invention provides a heater formed on a PCB using a PCB process so that the heater may have an accurate resistance. Further, the invention provides a heater that has an enhanced yield, has various shapes, and can be used in various uses.

Further, the invention uses two different substances on a PCB to form thermoelectric couple, thereby serving as a temperature sensor as well as a heater.

Further, the invention realizes at least one circuit using single PCB, thereby making a device adopting the PCB compact and slim.

The invention claimed is:

1. A method for manufacturing a heater using a PCB process, the method comprising the steps of:

forming a thin plate by coating substance that generates heat according to power supply on one side of an insulated board;

forming a masking pattern on an upper side of the insulated board, the masking pattern forming circuit patterns designed to have a heating resistor designed to have a constant resistance, a power supply terminal for supplying power to the heating resistor, a joining terminal of a sensor mount to which a sensor for measuring a heating temperature about a predetermined region of the heating resistor is mounted, and a sensor connecting terminal for causing the outside to read the temperature measured from the sensor;

etching to erode the insulated hoard that is formed with the masking pattern and generate the heater having the circuit patterns; and forming a insulating protecting film for protecting the patterns that are formed on the upper side of the insulated board, wherein the circuit pattern that is formed on the upper side of the insulated board is determined by the equation:

$$R=\rho L/A$$

where, $\rho$ is specific resistance of the heating resistor, L is length, and A is cross-sectional area.

2. A method according to claim 1, wherein resistance of the heating resistor is designed depending on input voltage, current, alternating current or direct current.

3. A method according to claim 1, wherein the step of forming the circuit patterns further comprises the step of forming circuit patterns different from the circuit pattern of the heating resistor on one side formed with the patterns and the other side, respectively.

4. A method according to claim 1, wherein substance coated on the insulated board is any one selected from the group consisting of copper, steel, nickel, chrome and alloy generated by compounding one substance into the pure metals.

5. A method according to claim 1, wherein the insulated board is coated with two different substances having high thermoelectromotive forces to form a heating resistor, respectively, the heating resistor generating heat according to whether power is supplied or not and forming thermoelectric couple, the insulated board being formed with a via hole for connecting the different substances.

6. A method according to claim 1, wherein the upper side and the lower side of the insulated board are coated with two different substances having high thermoelectromotive forces to form a heating resistor, respectively, the heating resistor generating heat according to whether power is supplied or not and forming thermoelectric couple, the insulated board being formed with a via hole for connecting the different substances.

7. A heater that is manufactured by a PCB process, the heater comprising:

an insulated board;

a heating resistor for generating heat with the amount of heat previously designed according to power supply, the heating resistor being formed by a circuit pattern designed to have a constant resistance on an upper side of the insulated board;

a power supply terminal for supplying the heating resistor with electric power;

a sensor mount that is mounted with a sensor for measuring heating temperature about a predetermined region of the heating resistor;

a sensor connecting terminal which is connected with the joining terminal to cause the outside to read the measured temperature; and an insulating protection film for protecting the heating resistor;

wherein a heating resistor pattern, a sensor mount joining pattern, and a sensor connecting terminal pattern are formed on an upper side of the insulated board by a masking process and a etching process, wherein the heating resistor is a resisting body, the circuit pattern of the heating resistor is determined by the equation:

$$R = \rho L/A$$

where, $\rho$ is specific resistance of the heating resistor, L is length, and A is cross-sectional area.

8. A heater according to claim 7, wherein resistance of the heating resistor is designed depending on input voltage, current, alternating current or direct current.

9. A heater according to claim 7, wherein a circuit pattern different from the circuit pattern of the heating resistor is formed on the other side of the insulated board as against one side of the insulated board formed with the circuit pattern of the heating resistor.

10. A heater according to claim 7, wherein substance coated on the insulated board is any one selected from the group consisting of copper, steel, nickel, chrome and alloy generated by compounding one substance into one of the above pure metals.

11. A heater according to claim 7, wherein the insulated board is coated with two different substances having high thermoelectromotive forces to form a heating resistor, respectively, the heating resistor generating heat according to whether power is supplied or not and forming thermoelectric couple, the insulated board being formed with a via hole for connecting the different substances.

12. A heater according to claim 7, wherein the upper side and the lower side of the insulated board are coated with two different substances having high thermoelectromotive forces to form a heating resistor, respectively, the heating resistor generating beat according to whether power is supplied or not and forming thermoelectric couple, the insulated board being formed with a via hole for connecting the different substances.

* * * * *